US012653421B2

(12) United States Patent

Groteke et al.

(10) Patent No.: US 12,653,421 B2
(45) Date of Patent: Jun. 16, 2026

(54) ABNORMAL GAIT DETECTION BASED ON 2D HUMAN POSE ESTIMATION

(71) Applicant: My Medical HUB Corporation, Safety Harbor, FL (US)

(72) Inventors: Walter M. Groteke, Safety Harbor, FL (US); Shoriful Islam, Dacca (BD); Barry Fitch, North Augusta, SC (US); Al Mehedi Hasan, Rajshahi (BD)

(73) Assignee: My Medical HUB Corporation, Safety Harbor, FL (US)

( * ) Notice: Subject to any disclaimer, the term of this patent is extended or adjusted under 35 U.S.C. 154(b) by 904 days.

(21) Appl. No.: 17/841,430

(22) Filed: Jun. 15, 2022

(65) Prior Publication Data

US 2022/0395195 A1 Dec. 15, 2022

Related U.S. Application Data

(60) Provisional application No. 63/210,623, filed on Jun. 15, 2021.

(51) Int. Cl.
*A61B 5/11* (2006.01)
*G06T 7/246* (2017.01)
*G06T 7/73* (2017.01)

(52) U.S. Cl.
CPC .............. *A61B 5/112* (2013.01); *G06T 7/251* (2017.01); *G06T 7/75* (2017.01)

(58) Field of Classification Search
CPC ..... A61B 5/112; A61B 5/0077; A61B 5/7267; G06T 7/251; G06T 7/75; G06T 2207/10016; G06T 2207/20081; G06T 2207/20084; G06T 2207/30232; G06T 2207/30196; G06T 7/0012; G06T 7/246
See application file for complete search history.

(56) References Cited

U.S. PATENT DOCUMENTS

| 10,842,415 B1 | 11/2020 | Jagannathan et al. |
| 2004/0228503 A1 | 11/2004 | Cutler |

(Continued)

OTHER PUBLICATIONS

A. Viswakumar, et al., "Human Gait Analysis Using OpenPose," 2019 Fifth International Conference on Image Information Processing (ICIIP), Shimla, India, 2019, pp. 310-314 (Year: 2019).*

(Continued)

*Primary Examiner* — Eric F Winakur
*Assistant Examiner* — Sienna C Pyle
(74) *Attorney, Agent, or Firm* — GREENBERG TRAURIG, LLP

(57) ABSTRACT

System and methods of using an Artificial Intelligence ("AI") trained model for classifying a patient's gait include receiving a video of a patient on the gait analysis device; classifying the patient's gait using a machine learning process on the gait analysis device; wherein the machine learning process is generated from an Artificial Intelligence ("AI") trained model comprising: a key point trained model configured to generate a set of key points on a patient's body; an Angle-Based Approach configured to use the set of key points to classify the patient's gait based on angle calculations between key points; and a Key Point Path Track-Based Approach configured to use the key points to classify the patient's gait based on a patient's stance phase and swing phase.

12 Claims, 20 Drawing Sheets

GAIT AI

(56) References Cited

U.S. PATENT DOCUMENTS

2012/0253234 A1  10/2012  Yang et al.
2019/0258851 A1*  8/2019  Rajan ..................... G06T 7/251

OTHER PUBLICATIONS

Ye et al., "Distinct Feature Extraction for Video-based Gait Phase Classification," 2019 IEEE ICME-2017 (Year: 2019).*
International Search Report and Written Opinion from International Appln. No. PCTUS2022033665 dated Oct. 26, 2022.

* cited by examiner

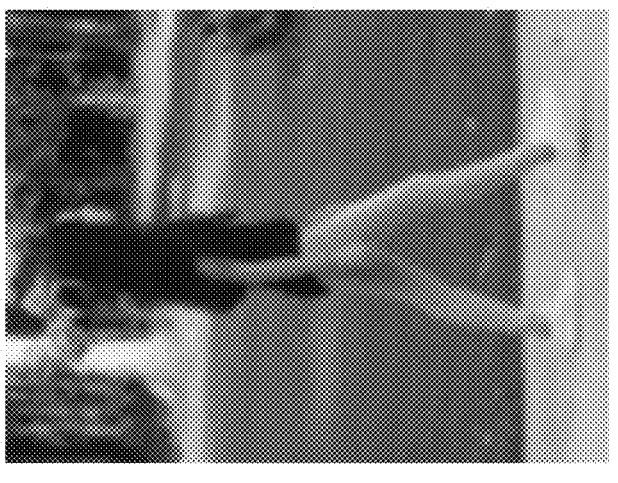
FIG. 1H
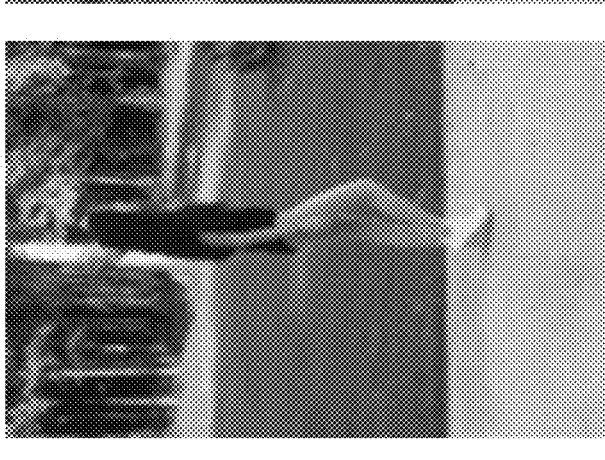
FIG. 1G
FIG. 1F
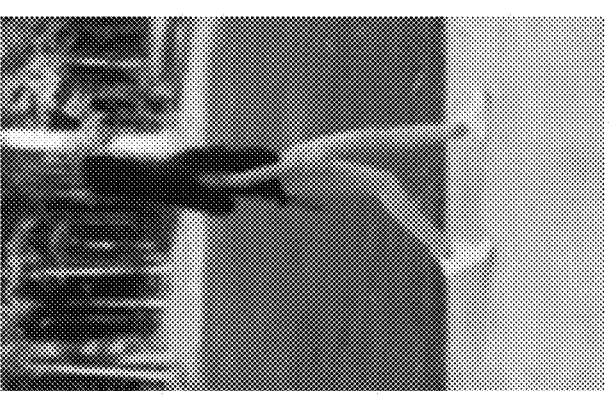
FIG. 1E

ABNORMAL GAIT DETECTION BASED ON 2D HUMAN POSE ESTIMATION

FIELD OF THE INVENTION

Embodiments of the present disclosure relate to computer systems and methods for automatically detecting abnormal gait in a patient.

BACKGROUND

Musculoskeletal disorders are injuries or disorders of the muscles, nerves, tendons, joints, cartilage, and spinal discs. People suffer from these disorders due to the nature of their lifestyle. Today people are less disposed toward physical work. As a result, the muscle, skeletal and/or nerve systems remain inactive and bodies start to persist in this state. In some instances, these changes can affect an individual's normal walking pattern. Walking anomalies, such as, shuffling, stiffing or unsteady walking are known as abnormal human gait.

Human gait analysis plays an important role in detecting musculoskeletal disorders. It can provide a quantitative measurement of biomechanical walking function, forming the basis of daily living activities. Gait holds the relationship between the upper and the lower body.

In some instances, gait is complex to analyze because every person has his/her own walking pattern and thus there can be many types of normal gait, as well as different types of abnormal gait.

SUMMARY

This summary is a high-level overview of various aspects and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification and any and all drawings.

Some embodiments of the present disclosure are directed to a system comprising a gait analysis device configured to receive a video of a patient transmitted from a sending device, wherein the gait analysis device comprises at least one memory, at least one processor configured to use a machine learning process for gait classification, and a display to output the gait classification. In some embodiments, the machine learning process is generated from a key point trained model configured to generate a set of key points on a patient's body, an Angle-Based Approach configured to use the set of key points to classify the patient's gait based on angle calculations between key points, and a Key Point Path Track-Based Approach configured to use the key points to classify the patient's gait based on a patient's stance phase and swing phase.

In some embodiments, the gait analysis device further comprises a frame extractor configured to extract frames from the video of the patient.

In some embodiments, the key point trained model is configured to generate the set of key points using the extracted frames.

In some embodiments, the key point trained model comprises a first key point trained model configured to predict a first set of key points on the patient's body using the extracted frames, a second key point trained model configured to predict a second set of key points on the patient's body using the extracted frames, and pose estimation configured to determine a third set of key points, wherein the third set of key points includes key points from the first set of key points and/or key points from the second set of key points.

In some embodiments, the first key point trained model is different from the second key point trained model.

In some embodiments, the set of key points comprises a key point for the nose, the left eye, the right eye, the left ear, the right ear, the left shoulder, the right shoulder, the left elbow, the right elbow, the left wrist, the right wrist, the left hip, the right hip, the left knee, the right knee, the left ankle, the right ankle, the left big toe, the right big toe, the left little toe, the right little toe, the left heel, the right heel, or any combination thereof.

In some embodiments, the angle calculations between key points include hip flexion, knee flexion, hip extension, knee extension, plantarflexion, dorsiflexion, or any combination thereof.

In some embodiments, the Key Point Path Track-Based Approach is configured to use signals detected for speed of the right ankle key point and the left ankle to classify the patient's gait based on a patient's stance phase and swing phase.

In some embodiments, the Key Point Path Track-Based Approach is configured to use signals detected of the distance between x-coordinates of ankle key point to classify the patient's gait based on a patient's stance phase and swing phase.

Some embodiments of the present disclosure are directed to a method. In some embodiments, the method comprises obtaining a gait analysis device, receiving a video of a patient on the gait analysis device, classifying the patient's gait using a machine learning process on the gait analysis device, and displaying the gait classification. In some embodiments, the machine learning process is generated from a key point trained model configured to generate a set of key points on a patient's body, an Angle-Based Approach configured to use the set of key points to classify the patient's gait based on angle calculations between key points; and a Key Point Path Track-Based Approach configured to use the key points to classify the patient's gait based on a patient's stance phase and swing phase.

Some embodiments of the present disclosure are directed to a method for automatically detecting abnormal gait in a patient.

In some embodiments, the method includes receiving, by a processor, a video showing a patient's gait, where the video comprises a plurality of film frames.

In some embodiments, the method includes detecting, by the processor, via a machine learning model, a plurality of coordinates indicative of a plurality of film frame locations, where each of the plurality of film frame locations shows a patient's joint.

In some embodiments, the method includes identifying, by the processor, based on the plurality of coordinates a first film frame showing a first heel strike and a second film frame showing a second heel strike performed by the subject.

In some embodiments, the first heel strike and the second heel strike denote a gait cycle.

In some embodiments, the method includes calculating, by the processor, a plurality of joint angles based on the plurality of coordinates, wherein the joint angles are calculated based on coordinates selected from the plurality of coordinates that are present in film frames that are between the first film frame and the second film frame.

In some embodiments, the method includes calculating, by the processor, a duration of a gait cycle stance phase and a duration of a gait cycle swing phase.

In some embodiments, the method includes determining, by the processor that the patient's gait is normal when the plurality of joint angles is within a predetermined range, and when a percentage of the duration of the gait cycle stance phase relative to the gait cycle swing phase is within a gait cycle stance phase normal range.

In some embodiments, the method includes determining, by the processor that the patient's gait is abnormal when the plurality of joint angles is not within the predetermined range, or the percentage of the duration of the gait cycle stance phase relative to the gait cycle swing phase is not within the gait cycle stance phase normal range.

BRIEF DESCRIPTION OF THE DRAWINGS

Some embodiments of the disclosure are herein described, by way of example only, with reference to the accompanying drawings. With specific reference now to the drawings in detail, it is stressed that the embodiments shown are by way of example and for purposes of illustrative discussion of embodiments of the disclosure. In this regard, the description taken with the drawings makes apparent to those skilled in the art how embodiments of the disclosure may be practiced.

FIGS. 1A-1H depict the stages of a gait cycle according to an exemplary embodiment of the present disclosure.

DETAILED DESCRIPTION

Figure 1D:
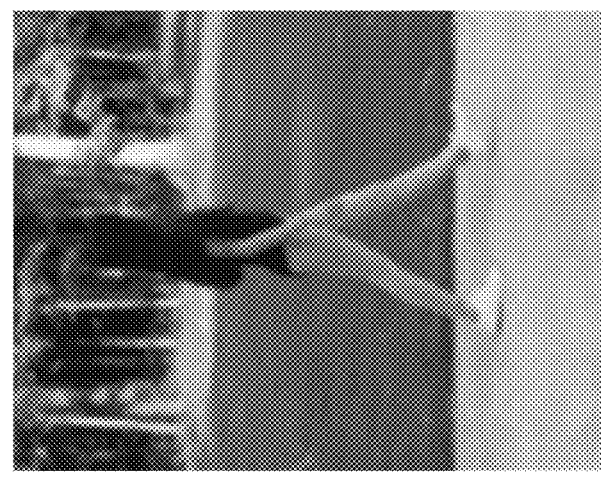

Among those benefits and improvements that have been disclosed other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, terms such as "comprising" "including," and "having" do not limit the scope of a specific claim to the materials or steps recited by the claim.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the terms "dynamically" and "automatically," and their logical and/or linguistic relatives and/or derivatives, means that certain events and/or actions can be triggered and/or occur without any human intervention. In some embodiments, events and/or actions in accordance with the present description can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

The method disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

In another form, a non-transitory article, such as a non-transitory computer readable medium, may be used with any of the examples mentioned above or other examples except that it does not include a transitory signal per se. It does include those elements other than a signal per se that may hold data temporarily in a "transitory" fashion such as RAM and so forth.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

As used herein, the term "hardware" may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

As used herein, the term "software" may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

As used herein, the term "patient" shall have a meaning of at least one individual.

As used herein, the term "gait" means a patient's walking pattern.

As used herein, the term "gait cycle" means the duration of time between two successive heel-strikes of the same foot. For example, in some embodiments, a gait cycle is the time between two successive heel-strikes of the right foot. In some embodiments, a gait cycle is the time between two successive heel-strikes of the left foot.

As used herein, the term "gait cycle stance phase" means the duration of time a foot is on the ground during a single gait cycle.

As used herein, the term "gait cycle swing phase" means the duration of time a foot is in the air during a single gait cycle.

As used herein, the term "normal gait" means cyclic, periodic and/or symmetric movement of the legs.

As used herein, the term "abnormal gait" means aperiodic, acyclic, and/or asymmetric movement of the legs.

As used herein, the term "gait classification" means whether a patient has a normal or abnormal gait.

As used herein, the term "pose estimation" means a method that predicts and tracks the location of a patient.

As used herein, "heel strike" means a stage of the gait cycle when the heel of the foot touches the ground.

As used herein, "mid stance" means a stage of the gait cycle when the tibia of the leg corresponding to the foot that is on the ground in a vertical position with respect to the ground.

As used herein, "toe off" means, a stage of the gait cycle when a front foot is on the ground and a back foot has a toe touching the ground.

As used herein, "mid swing," means a stage of the gait cycle when the tibia corresponding to the tibia of the leg corresponding to the foot that is on the ground is vertical to the ground while the other foot is swinging forward.

As used herein, "loading response" means a stage of the gait cycle when a front foot is on the ground and a back foot is initial lifted off the ground so as to begin to swing forward.

As used herein, "terminal stance" means a stage of the gait cycle when the heel of one foot moves vertically towards the ground.

As used herein, "initial swing" means a stage of the gait cycle when the hip, knee, and ankle of one leg are flexed to begin advancement of a foot from the back to the front.

As used herein, "terminal swing" means a stage of the gait cycle when the swinging foot touches the ground so as to reach the heel strike stage of the gait cycle.

As used herein, "hip flexion" means when the angle of the hip joint is less than 180 degrees. For example, if the angle of the hip joint is 160 degrees, then the hip flexion is 180–160=20 FLEX.

As used herein, "knee flexion" means when the angle of the knee joint is less than 180 degrees. For example, if the angle of the knee joint is 160 degrees, then the knee flexion is 180–160=20 FLEX.

As used herein, "hip extension" is when the angle of the hip joint is greater than 180 degrees. For example, if the angle of the hip joint is 200 degrees, then the hip extension is 200–180=20 EXT.

As used herein, "knee extension" is when the angle of the knee joint is greater than 180 degrees. For example, if the angle of the knee joint is 190 degrees, then the knee extension is 190–180=10 EXT.

As used herein, "plantarflexion" is when the angle of the ankle joint is greater than 90 degrees. For example, if the angle of the ankle joint is 100 degrees, then the plantarflexion is 100–90=10 PF.

As used herein, "dorsiflexion" is when the angle of the ankle joint is less than 90 degrees. For example, if the angle of the ankle joint is 80 degrees, then the dorsiflexion is 90–80=10 DF.

As used herein, the term "trained model" means an Artificial Intelligent ("AI") trained model.

As used herein, the term "Angle-Based Approach" shall mean classifying gait as normal or abnormal based on calculated angles between key points.

As used herein, the term "Key Point Path Track-Based Approach" shall mean classifying gait as normal or abnormal based on signals derived from the ankle key points during a patient's gait cycle stance phase and gait cycle swing phase.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor.

Some embodiments of the present disclosure are directed to computer systems and methods for automatically detecting a patient's abnormal gait. In some embodiments, the present disclosure provides exemplary inventive computer systems and computing devices configured to automatically and dynamically analyze a patient's gait cycle by applying one or more artificial intelligence ("AI")/machine learning techniques (e.g., algorithms) that have been trained (e.g., being continuously trained) to, for example without limitation, to perform at least one or more of the activities described herein.

In some embodiments, the present disclosure provides exemplary inventive computer systems and computing devices configured to automatically and dynamically detect musculoskeletal disorders in a patient based on an analysis of the patient's gait cycle by applying one or more artificial intelligence ("AI")/machine learning techniques (e.g., algorithms) that have been trained (e.g., being continuously trained) to, for example without limitation, to perform at least one or more of the activities described herein. In some embodiments, the musculoskeletal disorders that may by detected include, without limitation, cerebral palsy, stroke, traumatic brain injury, Parkinson's disease, lower limb amputation, or any combination thereof.

In some embodiments, methods for determining whether a patient has normal or abnormal gait using AI are disclosed. In some embodiments, the method includes receiving a video of a patient walking. In some embodiments, the video is received by hardware of a computer system. In some embodiments, the video includes a plurality of film frames. In some embodiments, the video is captured on camera having a frame rate per second ("fps") from 30 fps to 80 fps, from 40 fps to 80 fps, from 50 fps to 80 fps, from 60 fps to 80 fps, from 70 fps to 80 fps, from 30 fps to 70 fps, from 30 fps to 60 fps, from 30 fps to 50 fps, from 30 fps to 40 fps, from 40 fps to 70 fps, or from 50 fps to 60 fps.

In some embodiments, the method includes dividing the video into a sequence of frames. In some embodiments, the sequence of frames is based on the frame rate per second at which the video is captures. In some embodiments, the method includes extracting video metadata.

In some embodiments, the video of the patient walking shows the patient's gait cycle. In some embodiments, the video of the patient walking shows at least 2 gait cycles, at least 3 gait cycles, at least 4 gait cycles, at least 5 gait cycles, at least 6 gait cycles, at least 7 gait cycles, at least 8 gait cycles, at least 9 gait cycles, or at least 10 gait cycles. In some embodiments, the video of the patient walking shows from 1 to 10 gait cycles, from 1 to 9 gait cycles, from 1 to 8 gait cycles, from 1 to 7 gait cycles, from 1 to 6 gait cycles, from 1 to 5 gait cycles, from 1 to 4 gait cycles, from 1 to 3 gait cycles, from 1 to 2 gait cycles, from 2 to 10 gait cycles, from 3 to 10 gait cycles, from 4 to 10 gait cycles, from 5 to 10 gait cycles, from 6 to 10 gait cycles, from 7 to 10 gait cycles, from 8 to 10 gait cycles, from 9 to 10 gait cycles, from 2 to 9 gait cycles, from 3 to 8 gait cycles, from 4 to 7 gait cycles, or from 5 to 6 gait cycles.

In some embodiments, the plurality of film frames in the video show the patient's joints. In some embodiments a first film frame shows a first heel strike and a second film frame shows a second heel strike.

In some embodiments, the method includes determining whether the patient has normal or abnormal gait based on AI that has been trained with one or more inputs. In some embodiments, the inputs include rules and/or methodologies for recognizing normal gait. In some embodiments, the rules and/or methodologies include the Angled-Based Approach, the Key Point Path Track-Based Approach, or any combination thereof.

Figure 1C:
Figure 1C:
Figure 1B:
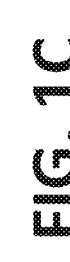
Figure 1B:
Figure 1A:
Figure 1A:

In some embodiments, the Angle-Based Approach includes rules and/or methodologies for recognizing normal gait includes values associated with the range of motion of joints of the lower extremities at different stages of the gait cycle. For example, in some embodiments the inputs include rules based on flexion and/or extension of the knee, hip, ankle, or any combination thereof, at different stages of the gait cycle. In some embodiments, the different stages of the gait cycle include heel strike, loading response, mid stance, terminal stance, toe off, initial swing, mid-swing, and terminal swing. FIGS. 1A-1H depict the different stages of the gait cycle. FIG. 1A depicts the heel strike stage of the gait cycle. FIG. 1B depicts the loading response stage of the gait cycle. FIG. 1C depicts the mid stance stage of the gait cycle. FIG. 1D depicts the terminal stance stage of the gait cycle. FIG. 1E depicts the toe off stage of the gait cycle. FIG. 1F depicts the initial swing stage of the gait cycle. FIG. 1G depicts the mid-swing stage of the gait cycle, and FIG. 1H depicts the terminal swing stage of the gait cycle.

In some embodiments, inputs into the trained AI model for determining whether a patient has normal or abnormal gait using the Angle-Based Approach include rules based on flexion and extension of the knee, ankle, and/or hip joints during at least the heel strike stage, the mid stance stage, the toe off stage, and the mid swing stage of the gait cycle.

In some embodiments, the inputs include a rule that normal gait corresponds to hip flexion and/or hip extension during the heel strike stage of the gait cycle from 1 FLEX to 50 FLEX, including, without limitation, from 5 FLEX to 45 FLEX.

In some embodiments, the inputs include a rule that normal gait corresponds to knee flexion and/or knee extension during the heel strike stage of the gait cycle from 35 FLEX to 15 EXT, including, without limitation, from 30 FLEX to 10 EXT.

In some embodiments, the inputs include a rule that normal gait corresponds to ankle dorsiflexion and/or plantarflexion during the heel strike stage of the gait cycle from 25 DF to 10 PF, including, without limitation, from 25 DF to 5 PF or from 20 DF to 5 PF.

In some embodiments, the inputs include a rule that normal gait corresponds to hip flexion and/or hip extension during the mid stance stage of the gait cycle from 25 FLEX to 20 EXT, including, without limitation, from 20 FLEX to 15 EXT.

In some embodiments, the inputs include a rule that normal gait corresponds to knee flexion and/or knee extension during the mid stance stage of the gait cycle from 30 FLEX to 10 EXT, including, without limitation, from 25 FLEX to 5 EXT.

In some embodiments, the inputs include a rule that normal gait corresponds to dorsiflexion and/or plantarflexion during the mid stance stage of the gait cycle from 20 DF to 10 PF, including, without limitation, from 20 DF to 5 PF or from 15 DF to 5 PF.

In some embodiments, the inputs include a rule that normal gait corresponds to hip flexion and/or hip extension during the toe off stage of the gait cycle from 20 FLEX to 40 EXT, including, without limitation, from 20 FLEX to 35 EXT or from 15 FLEX to 35 EXT or from 15 FLEX to 40 EXT.

In some embodiments, the inputs include a rule that normal gait corresponds to knee flexion and/or knee extension during the toe off stage of the gait cycle from 10 FLEX to 70 FLEX, including, without limitation, from 15 FLEX to 65 FLEX.

In some embodiments, the inputs include a rule that normal gait corresponds to dorsiflexion and/or plantarflexion during the toe off stage of the gait cycle from 25 DF to 25 PF, including, without limitation from 20 DF to 25 PF or from 20 DF to 20 PF.

In some embodiments, the inputs include a rule that normal gait corresponds to hip flexion and/or hip extension during the mid swing stage of the gait cycle from 45 FLEX to 5 EXT, including, without limitation, from 40 FLEX to 5 EXT.

In some embodiments, the inputs include a rule that normal gait corresponds to knee flexion and/or knee extension during the mid swing stage of the gait cycle from 20 FLEX to 90 FLEX, including, without limitation, from 25 FLEX to 85 FLEX.

In some embodiments, the inputs include a rule that normal gait corresponds to dorsiflexion and/or plantarflexion during the mid swing stage of the gait cycle from 20 DF to 15 PF, including, without limitation, from 15 DF to 10 PF.

In some embodiments, the AI model for determining whether a patient has normal or abnormal gait using the Angle-Based Approach includes pose estimation. In some embodiments, pose estimation includes estimating the location of key points in a video of a patient's gait cycle to determine the maximum and minimum horizontal and vertical distances of the key points. In some embodiments, pose estimation includes detecting coordinates of the key points. In some embodiments, detecting the coordinates is performed by hardware of a computer system. In some embodiments, detecting the coordinates is performed via a machine learning model.

In some embodiments, pose estimation may be configured to estimate an X coordinate and a Y coordinate for at least twenty-two key-points of a patient's body. In some embodiments, the at least twenty-two key-points include, without limitation, the patient's nose, left eye, right eye, left ear, right ear, left shoulder, right shoulder, left elbow, right elbow, left wrist, right wrist, left hip, right hip, left knee, right knee, left ankle, right ankle, left big toe, left heel, right big toe, right little toe, and right heel.

In some embodiments, pose estimation may be determined using Computer Vision. In some embodiments, pose estimation may be determined using custom-trained models including HigherHR Net framework, Detectron2 library, or any combination thereof. In some embodiments, pose estimation may be determined using at least two custom-trained models. In some embodiments, a first custom-trained model may be used to estimate a first set of key points. In some embodiments, a second-custom trained model may be used to estimate a second set of key points.

In some embodiments, the first set of key points includes an estimate of an X coordinate and a Y coordinate for at least twenty-three key-points of a patient's body. In some embodiments, the at least twenty-three key-points include, without limitation, the patient's nose, left eye, right eye, left ear, right ear, left shoulder, right shoulder, left elbow, right elbow, left wrist, right wrist, left hip, right hip, left knee, right knee, left ankle, right ankle, left big toe, left little toe, left heel, right big toe, right little toe, and right heel.

In some embodiments, the second set of key points includes an estimate of an X coordinate and a Y coordinate for the at least twenty-three key-points of a patient's body. In some embodiments, the at least twenty-three key-points include, without limitation, the patient's nose, left eye, right eye, left ear, right ear, left shoulder, right shoulder, left elbow, right elbow, left wrist, right wrist, left hip, right hip, left knee, right knee, left ankle, right ankle, left big toe, left little toe, left heel, right big toe, right little toe, and right heel.

In some embodiments, pose estimation may determine a third set of the at least twenty-three key points of the patient's body based on accuracy of the key points in the first set of key points and the second set of key points. For example, in some embodiments pose estimation compares accuracy of the key point for the patient's nose in the first set of key points and the key point for the patient's nose in the second set of key points and choses the most accurate of these two key points as the key point for the patient's nose in the third set of key points. In some embodiments, pose estimation does this comparison for each key point in the first set of key points and in the second set of key points to compile the third set of key points.

In some embodiments, the AI trained model using the Angle-Based Approach calculates a plurality of joint angles based on the detected or estimated coordinates of the key points. In some embodiments, the AI trained model calculates a plurality of joint angles based on the detected or estimated coordinates of the key points in the first set of key points, in the second set of key points, in the third set of key points, or any combination thereof. In some embodiments, the joint angles correspond to the hip joint, the knee joint, the ankle joint, toe joints, the shoulder joint, the elbow joint, or any combination thereof. In some embodiments, the joint angles may be used to determine hip flexion, hip extension, knee flexion, knee extension, ankle plantarflexion, and/or ankle dorsiflexion during stages of the gait cycle.

In some embodiments, calculating the plurality of joint angles may include using the coordinates of the first set of key points, of the second set of key points, of the third set of key points, or any combination thereof, to calculate the patient's hip angle, knee angle, heel angle, or any combination thereof. In some embodiments, calculating the patient's hip angle may include calculating the angle between the patient's shoulder joint, hip joint, and knee joint. In some embodiments, calculating the knee angle may include calculating the angle between the patient's hip joint, knee point, and ankle point.

In some embodiments, calculating the heel angle may include calculating the angle between the patient's knee point, heel point, and toe.

In some embodiments, the method using the Angle-Based Approach may include using the coordinates of the first set of key points, the second set of key points, the third set of key points, or any combination thereof, to detect the patient's gait cycle. In some embodiments, the method may include using the coordinates of the key points to detect the patient's gait cycle stance phase. In some embodiments, the method may include using the coordinates of the key points to detect the patient's gait cycle swing phase. In some embodiments, using the coordinates of the key points to detect the patient's gait cycle may include calculating maximum horizontal distance of an ankle point during two consecutive heel strikes. In some embodiments, using the plurality of coordinates to detect the patient's gait cycle may including calculating the maximum vertical distance of an ankle point during two consecutive heel strikes.

In some embodiments, the Angle-Based Approach may not detect the gait cycle phases accurately all the time. In some embodiments, a second approach namely the Key Point Path Track-Based Approach may be integrated with the Angle-Based Approach to classify a patient's gait.

In some embodiments, the method includes using the Key Point Path Track-Based Approach to determine whether a patient has normal or abnormal gait. In some embodiments, the Key Point Path Track-Based Approach may include using detected key points to calculate the duration of the patient's gait cycle. In some embodiments, calculating the duration of the patient's gait cycle may be performed by hardware in the computer system. In some embodiments, calculating the duration of the gait cycle may including calculating the duration of the patient's gait cycle stance phase and calculating the duration of the patient's gait cycle swing phase. In some embodiments, calculating the duration of the gait cycle may include calculating the duration of the patient's gait cycle stance phase and gait cycle swing phase with respect to the patient's left foot. In some embodiments, calculating the duration of the gait cycle may include calculating the duration of the patient's gait cycle stance phase and gait cycle swing phase with respect to the patient's right foot.

In some embodiments, the Key Point Track-Based Approach may include calculating the average duration of the patient's gait cycle stance phase. In some embodiments, the method may include calculating the average duration of the patient's gait cycle swing phase. In some embodiments, the method may include calculating the average duration of the patient's gait cycle. In some embodiments, the method may include calculating the average length of the patient's gait cycle. In some embodiments, the method may include calculating the average speed of the patient's gait cycle.

In some embodiments, calculating the average duration, average length, average speed or any combination thereof of the patient's gait cycle may include calculating at least one signal using the detected left ankle key point and/or the detected right ankle key point. In some embodiments, the at least one signal may include (1) a signal based on the difference in the x-coordinate of the left ankle key point and the x-coordinate of the right ankle key point; (2) a signal based on the displacement of the ankle key point for the primary leg; and (3) a signal based on the displacement of the ankle key point for the opposite leg. In some embodiments, when a patient walks from left to right, the right left is the primary leg and the left leg is the opposite leg. In some embodiments, when a patient walks from right to left, the left leg is the primary leg and the right leg is the opposite leg.

In some embodiments, the detected signals described above may be used to calculate the average duration, average length, average speed or any combination thereof of the patient's gait cycle may include smoothing at least one of the signals. In some embodiments, smoothing at least one of the signals may include using the interquartile range for discarding outliers, a custom-trained one and two degree smoothing method, the savitzky-golay filter, or any combination thereof. In some embodiments, the average duration, average length, average speed, or any combination thereof, of the patient's gait cycle may be detected after smoothing of at least one of the signals as described below.

In some embodiments, the three signals may be referred to as "feature signals" or fs. In some embodiments, the signal based on the differences in the x-coordinate of the left ankle key point and the x-coordinate of the right ankle key point is fs1. In some embodiments, the raw signal of difference in ankles in x-axis is captured using Eq. (1).

$$ankle\_difference[i]=|left\_ankle[i].x-right\_ankle[i].x| \qquad (1)$$

In some embodiments, "keypoint_name[frame_index].x" denotes the coordinate value of a key point in the x-axis for the particular frame with "frame_index" and "keypoint_ name[frame_index].y" to do the same in the y-axis. In some embodiments, in Eq. (1), two pipes or '| . . . |' refers to modulus operation i.e., absolute difference.

Figures 9A, 9B:
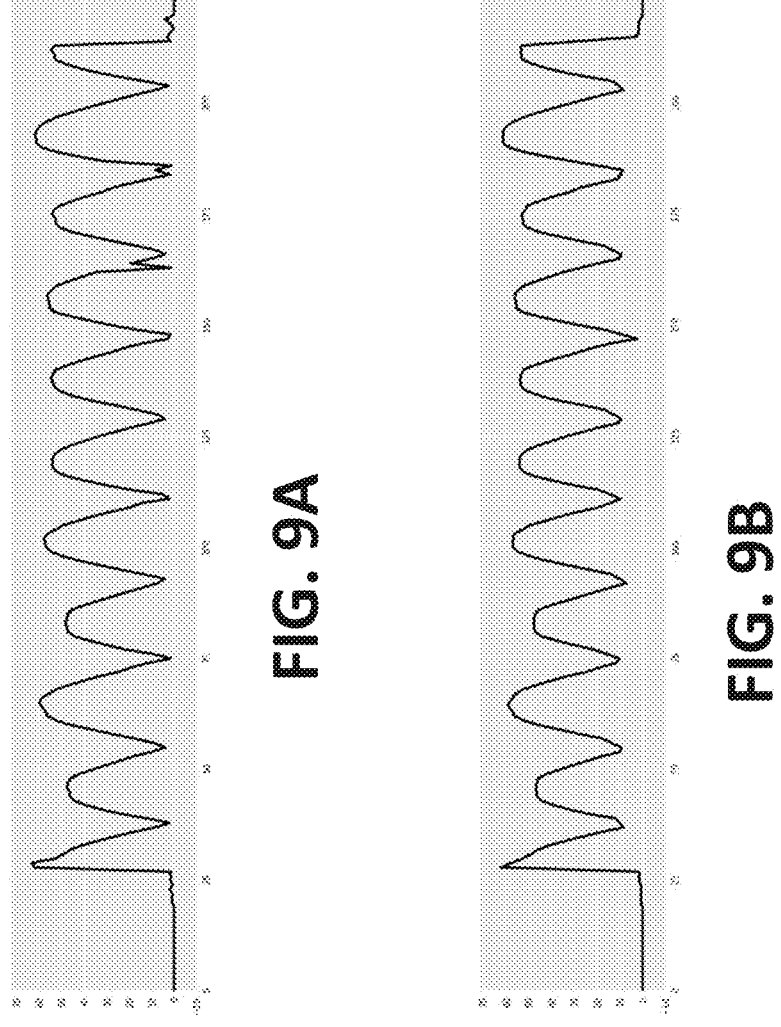
FIGS. 9A-9D depict exemplary signals according to an embodiment of the present disclosure.

FIGS. 9A-9D depict exemplary signals for fs. FIG. 9A depicts an exemplary raw signal captured by Eq. (1). FIG. 9B depicts an exemplary smoothed signal of the raw signal in FIG. 9A with one degree of smoothing. In some embodiments, one degree smoothing, for any value from the signal, first includes determining whether a value is between its adjacent values in the signal. If so, then the value is kept in the smoothened signal. Otherwise, the average of the adjacent values is used in the smoothened signal using Eq. (2).

$$raw\_signal[i]=(raw\_signal[i-1]+raw\_signal[i+1])/2 \qquad (2)$$

Figure 9C:
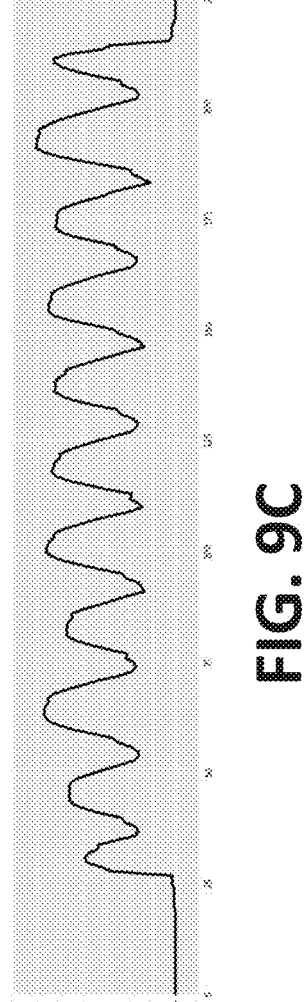

FIG. 9C depicts an exemplary smoothed signal of the signal in FIG. 9B with two degree smoothing. In some embodiments, two degree smoothing, for any value from the signal, first includes checking if a value is in between the average of the previous two values and the average of the next two values. If so, then the value is kept as it is. Otherwise, that value is replaced with the average of the average of the previous two values and the average of next two values, which is defined by Eq. (3). In some embodiments, if raw_signal[i] is not in range of (raw_signal[i−2]+raw_signal[i−1])/2 and raw_signal[i+1]+raw_signal[i+2])/2, considering one of the values of to be maximum and one to be minimum of the range, then the value of raw_signal[i] is replaced using the following equation (Eq. (3)) for two degree smoothing.

$$raw\_signal[i]=((raw\_signal[i-2]+raw\_signal[i-1])/2+ \\ (raw\_signal[i+1]+raw\_signal[i+2])/2)/2 \qquad (3)$$

Figure 9D:
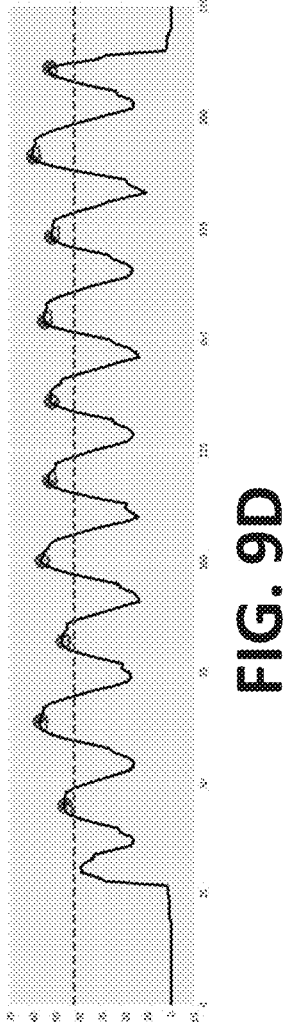

FIG. 9D depicts an exemplary embodiment of heel strike detection at each peak using the two degree smoothed signal of FIG. 9C. For example, in some embodiments, heel strikes are considered peaks at y-axis with a threshold above 70% of the range between the minimum value and the maximum value; from the minimum value. In some embodiments, a peak finding algorithm namely find_peaks( ) which is provided in the signal module from scipy library may be used. In some embodiments, this function takes a 1-D array and finds all local maxima by simple comparison of neighboring values. In some embodiments, a threshold of minimum horizontal distance of 10 may be used to make sure that no two peaks are in between 10 adjacent values in the given signal. In FIG. 9D, the triangle refers to the heel strike frames detected by a human expert and the red circle refers to prediction by an exemplary system of the present disclosure.

In some embodiments, the signal based on the displacement of the right ankle key point may be fs2 and the signal based on the displacement of the left ankle key point may be fs3. In some embodiments, the signals based on displacement of the right and left ankles may refer to speed of the right ankle and speed of the left ankle, respectively. In some embodiments, an algorithm may be used to determine the orientation for signal adjustment. In some embodiments, "orientation" refers to whether the patient is moving left to right or right to left in the video. In some embodiments, key points (discussed above) may be compared to determine the orientation. For example, in some embodiments, key points of the ankle may be compared to key points of the ear and nose to determine orientation. If the nose point is on the right side of the ear point, then the patient is walking left to right, and if the nose point is on the left side of the ear point, the patient is walking right to left. If the person is walking left to right, then the right lateral view of the person is clearly visible in the camera, and the right leg is considered as the primary leg (and the left leg is considered as the opposite leg) for the calculation. Similarly, if the person is walking right to left, then the person's left lateral view is visible, and the left leg is considered as the primary leg (and the right leg is considered as the opposite leg) for the calculation.

In some embodiments, the first heel strike made by the primary leg is the beginning point of signal processing or calculation for the speed of the ankles, and the calculation stops at the last heel strike made by the primary leg. For example, in some embodiments, the indexes before the first heel strike and after the last heel strike are filled with the value 0. The other values are calculated as the distances passed in the last five frames. In some embodiments, a comparison is made between the x-coordinate value of the key point of the ankle in a first frame to an x-coordinate value of the key point of the ankle in a second frame. In some embodiments, the second frame may be 10 frames, 9 frames, 8 frames, 7 frames, 6 frames, 5 frames, 4 frames, 3 frames, 2 frames, or 1 frame back from the first frame. In some embodiments, the difference between the x-coordinate of the ankle in the first frame and the x-coordinate of the ankle in the second is used as the value in the signal. In some embodiments, this is calculated using Eq. (4) and Eq. (5).

$$\text{left\_speed} = |\text{left\_ankle}.x[i] - \text{left\_ankle}.x[i-5]|/5 \qquad (4)$$

$$\text{right\_speed} = |\text{right\_ankle}.x[i] - \text{right\_ankle}.x[i-5]|/5 \qquad (5)$$

In the exemplary embodiment of Eq. (4) and Eq. (5) above, left_ankle is x[i] is the x-coordinate of the first frame's left ankle key point and left_ankle.x[i−5] is the x-coordinate of the second frame's left ankle key point. In the exemplary embodiment of Eq. (4) and Eq. (5), the second frame is 5 frames back from the first frame.

Figures 10A, 10B:
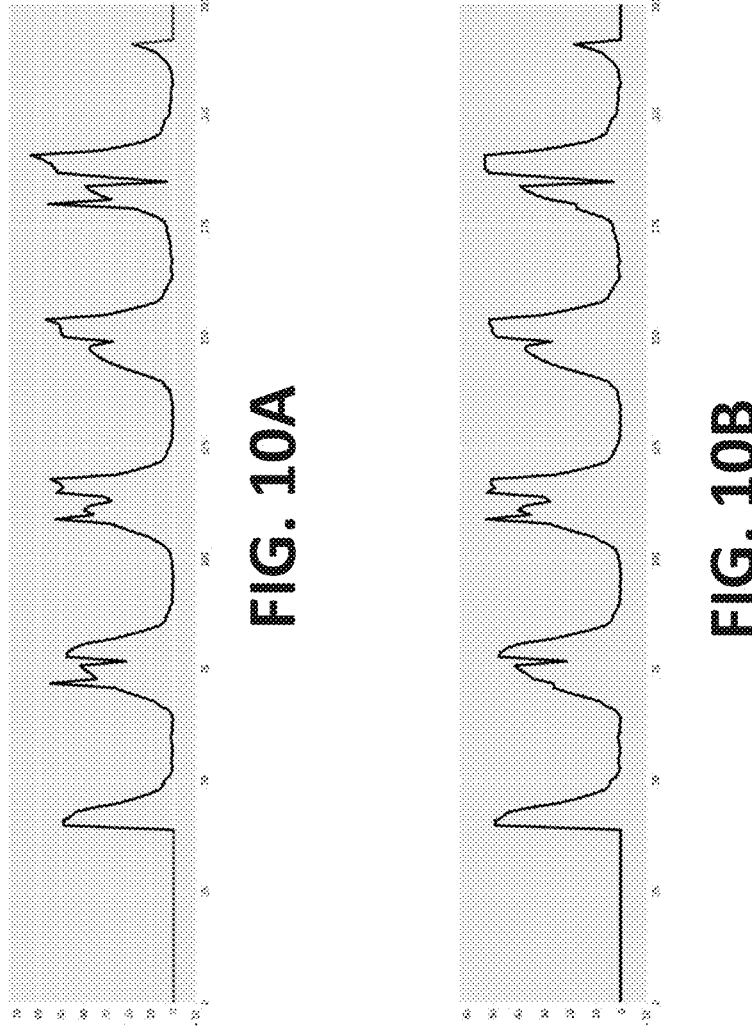
FIGS. 10A-10G depict exemplary signals according to an embodiment of the present disclosure.

FIGS. 10A-10G and 11A-11G depict exemplary signals for fs2 and fs3, respectively. FIGS. 10A and 11A depict exemplary embodiments of the raw signals.

FIGS. 10B and 11B depict exemplary embodiments of the raw signals of 10A and 11A with outliers discarded. In some embodiments, after the raw signals are calculated, there might be outliers due to the instability of the camera or misprediction of the body key points. In some embodiments, the interquartile range (IQR) of the raw signals is calculated using Eq. (6) to Eq. (8). In some embodiments, a value may be an outlier if the value of the signal exceeds the range $Q1-1.5\times IQR$ to $Q3+1.5\times IQR$. In some embodiments, if any value is regarded as outlier, that value may be replaced with the value with the value at the previous index of the signal.

$$Q1 = (n+1) \times \tfrac{1}{4} \qquad (6)$$

$$Q3 = (n+1) \times \tfrac{3}{4} \qquad (7)$$

$$IQR = Q3 - Q1 \qquad (8)$$

Figures 10C, 10D:
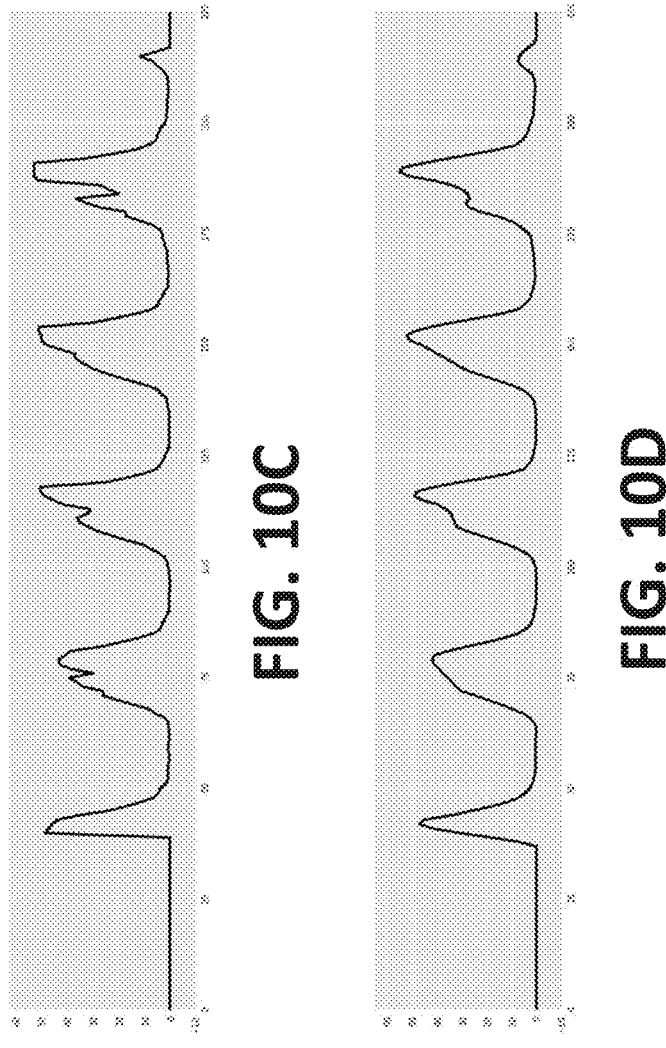
Figures 10E, 10F:
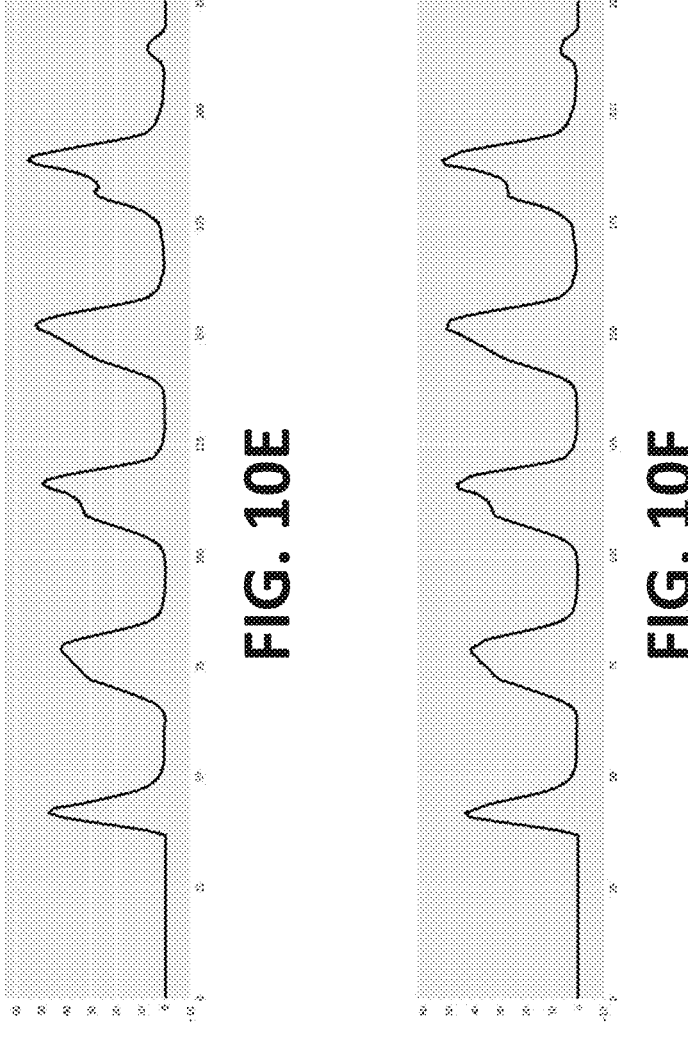
Figures 11A, 11B:
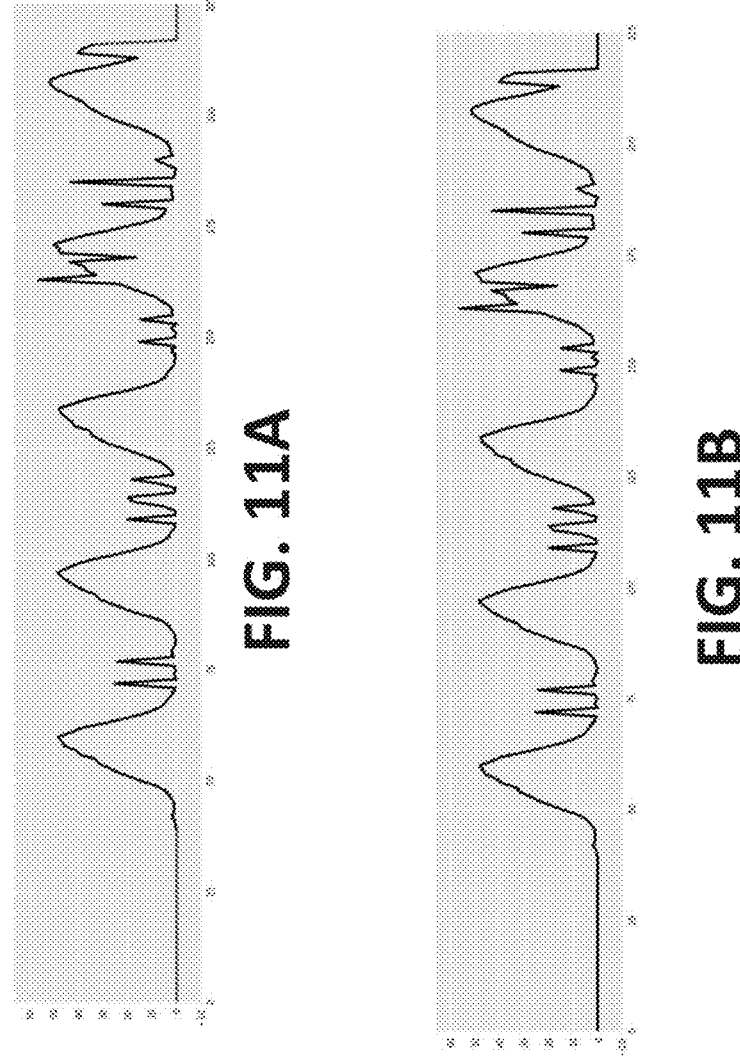
FIGS. 11A-11G depict exemplary signals according to an embodiment of the present disclosure.
Figures 11C, 11D:
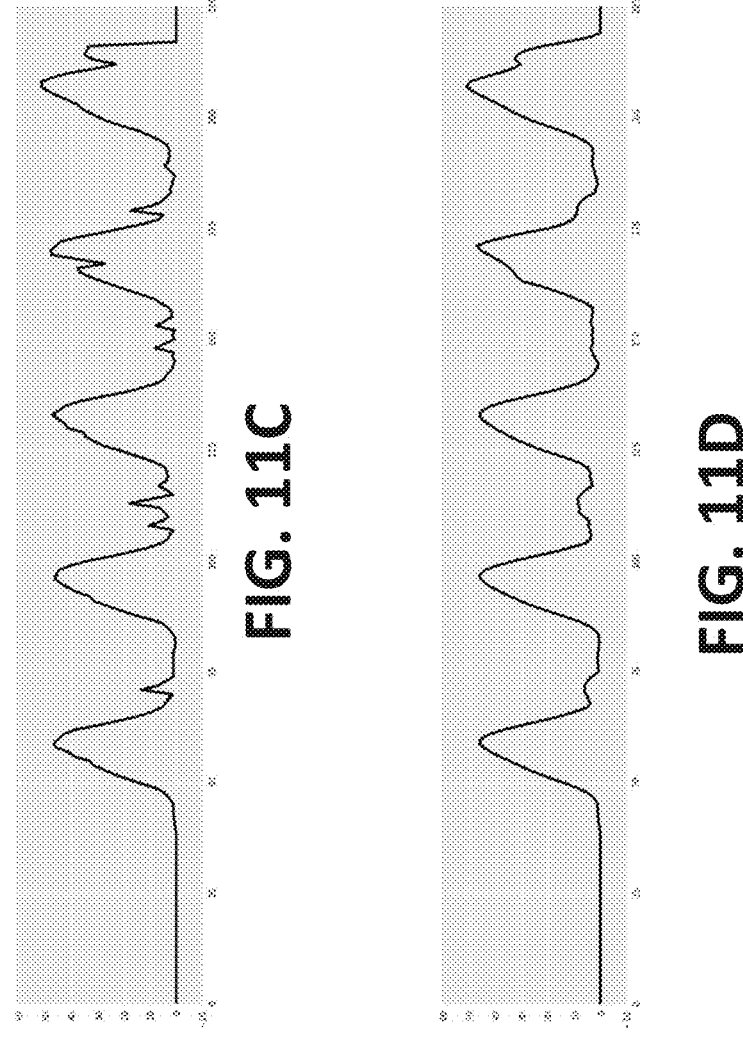
Figures 11E, 11F:
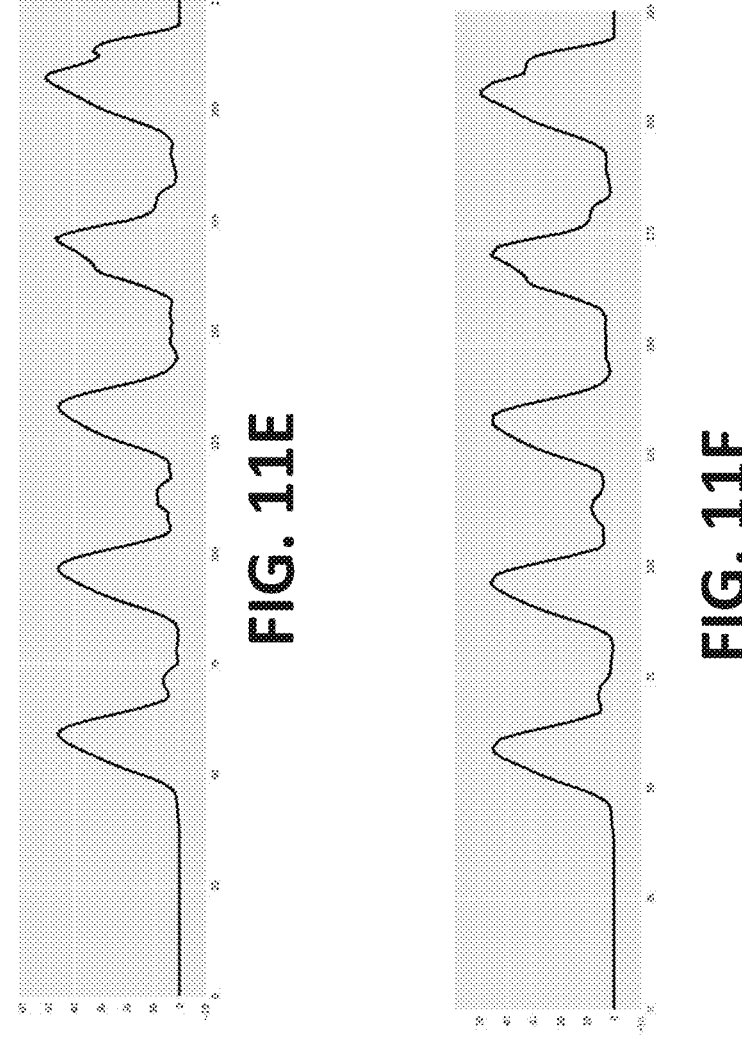
Figures 10G, 11G:
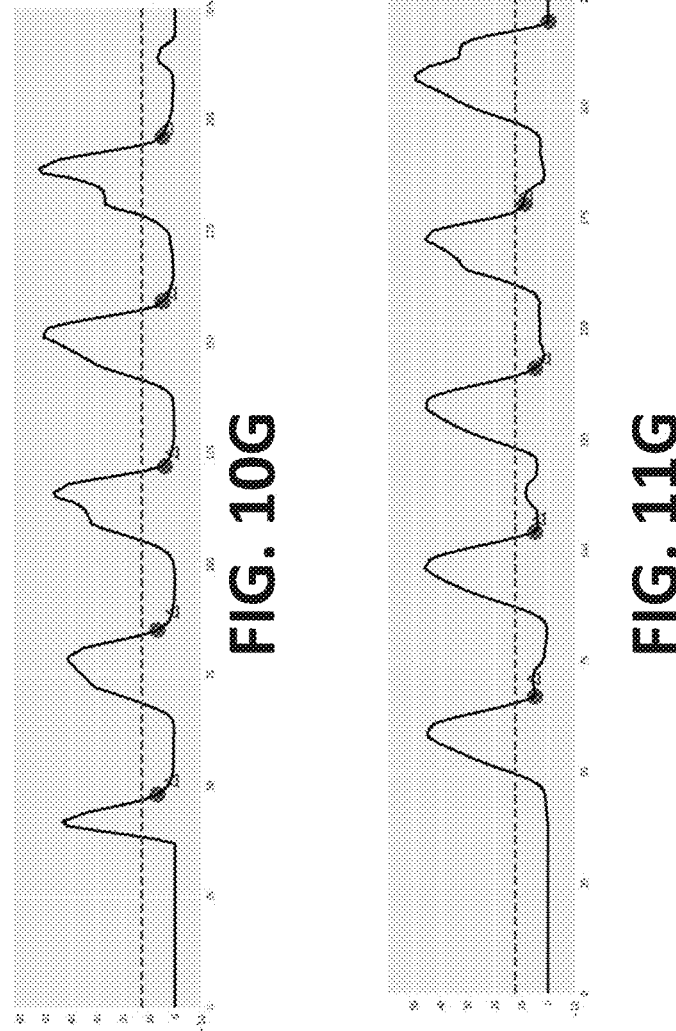

FIGS. 10C and 11C depict an exemplary smoothed signals of the signals in FIGS. 10B and 11B with one and two degree smoothing described above. FIGS. 10D and 11D depict smoothing of the signals in FIGS. 10C and 11C using a Savitzky-Golay filter. In some embodiments, as the Savitzky-Golay filter smoothens the signal using interpolation technique, there might be negative values in the smoothed signal. In some embodiments, to avoid the negative values, the negative values are replaced with "0". FIGS. 10E and 11E depict exemplary embodiments of the signals of FIGS. 10D and 11D with the negative values replaced with "0". In some embodiments, the signals of FIGS. 10E and 11E are then smoothed again with the one and two degree smoothing described above. FIGS. 10F and 11F depict exemplary embodiments of the signals of FIGS. 10E and 11E smoothed a second time with one and two degree smoothing. FIGS. 10G and 11G depict exemplary embodiments of the detected swing phases for each ankle using the smoothed signals of FIGS. 10F and 11F, where the trials indicate the actual values detected by a human expert of the start of each swing phase and the circles indicate the predicted values by an exemplary system of the start of each swing phase.

In some embodiments, fs1, fs2, fs3, or any combination thereof, may be used to determine the patient's gait cycle swing phase and gait cycle stance phase.

In some embodiments, the method includes determining whether the patient has normal gait. In some embodiments, determining whether the patient has normal gait is performed by hardware in the computer system. In some embodiments, determining whether the patient has normal gait includes determining whether each of the calculated joint angles are within normal ranges of motion using the Angle-Based Approach. In some embodiments, the normal ranges of motion correspond to the rules for hip flexion, hip extension, knee flexion, knee extension, ankle dorsiflexion, and ankle plantarflexion during at least the heel strike stage, the mid stance stage, the toe off stage, and the mid swing stage of the gait cycle, which are described herein.

In some embodiments, determining whether the patient has normal gait includes determining whether a percentage of the gait cycle stance phase is within the gait cycle stance phase normal range using the Angle-Based Approach, the Key Point Path Track-Based Approach, or any combination thereof. In some embodiments, the gait cycle stance phase normal range is 50% to 70% of the duration of the gait cycle. In some embodiments, determining whether the patient has normal gait includes determining whether a percentage of the gait cycle swing phase is within the gait cycle swing phase normal range using the Angle-Based Approach, the Key Point Path Track-Based Approach, or any combination thereof. In some embodiments, the gait cycle swing phase normal range is 30% to 50% of the duration of the gait cycle.

Figure 12:
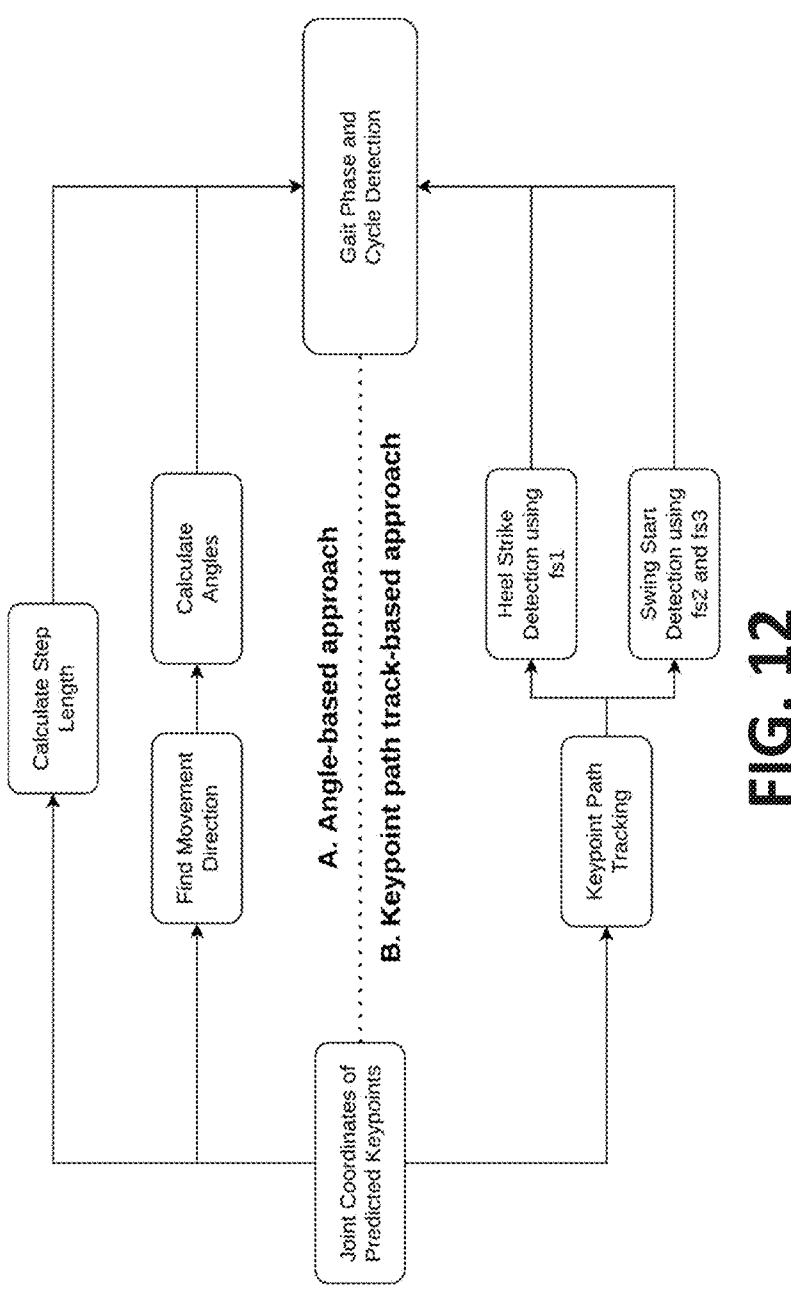
FIG. 12 depicts an Integrated Approach for classifying a patient's gait according to an exemplary embodiment of the present disclosure.

In some embodiments, determining whether the patient has normal gait includes using both the Angle-Based Approach and the Key Point Path Track-Based Approach, i.e., an Integrated Approach (FIG. 12). In some embodiments, the Integrated Approach includes averaging results of the Angle-Based Approach and the Key Point Path Track-Based Approach, concentrating or voting to give preference to a particular result obtained from the Angle-Based Approach, concentrating or voting to give preference to a particular result from the Key Point Path Track-Based Approach, or any combination thereof.

In some embodiments, the method includes a calibration process. In some embodiments, the calibration process occurs prior to determining whether the patient has normal or abnormal gait. In some embodiments, the calibration process includes receiving an input video of the patient and receiving the patient's height. In some embodiments, the calibration process includes determining the best film frame of the video. In some embodiments, the calibration process includes calculating the distance per pixel of the best film frame based on the patient's height.

The present disclosure will now be described with reference to non-limiting exemplary embodiments depicted in FIGS. 2-8 and 13.

Figure 2:
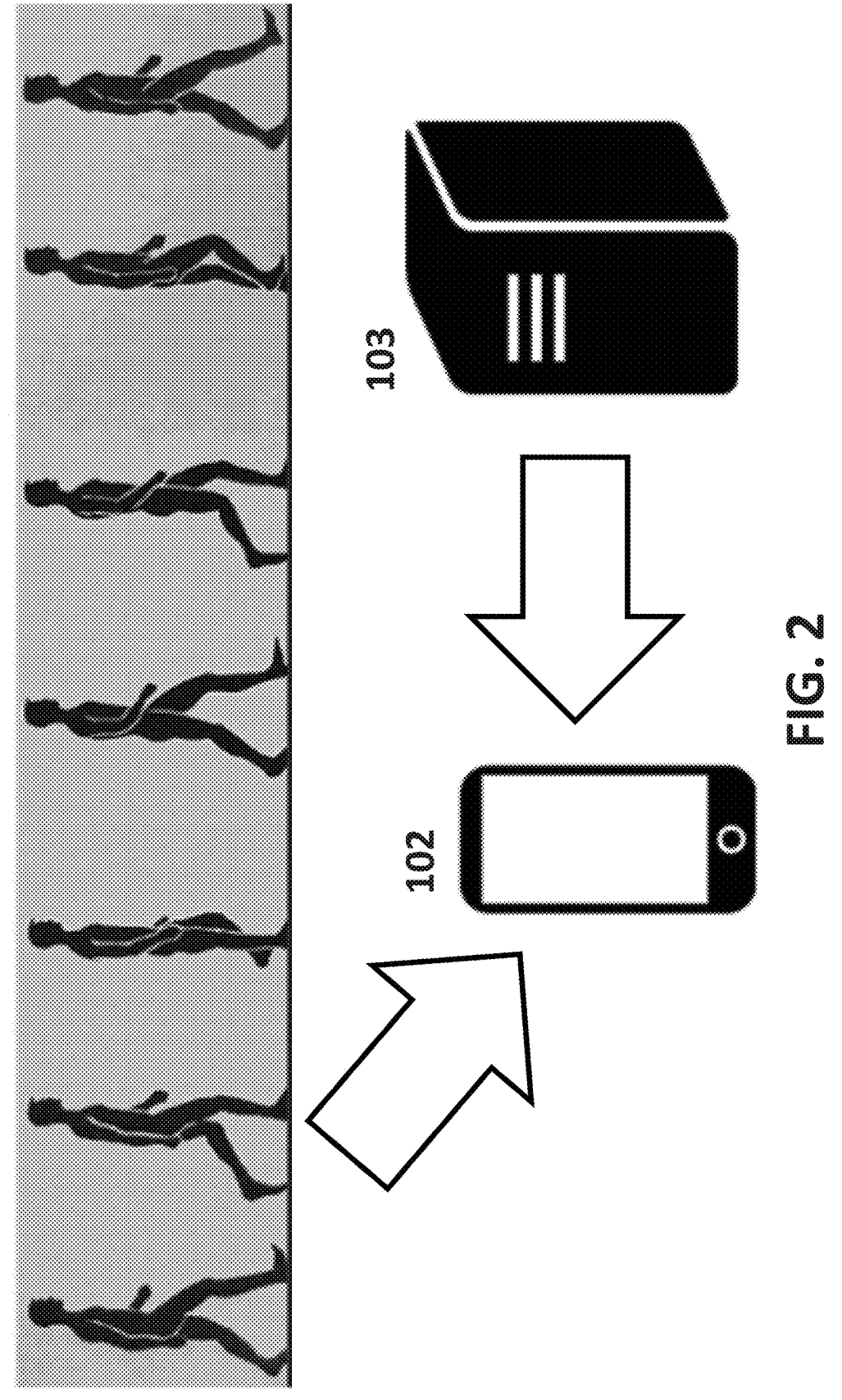
FIG. 2 depicts an exemplary operational environment of at least some embodiments of the present disclosure.

FIG. 2 depicts an exemplary operational environment of at least some embodiments of the present disclosure. As shown in FIG. 2, the exemplary operational environment may include user(s) 101, mobile device(s) 102 and server(s)

103. Other devices may also be included. For example, the mobile device(s) 102 may include any appropriate type of mobile devices, such as mobile phones, smartphones and tablets or any personal computer. For example, the server(s) 103 may include suitable type of server computer or a plurality of server computers for providing technical ability to perform external calculations and simulations to improve face tracking and/or age detection models. In some embodiments, the user(s) 101 may interact with the mobile device(s) 102 by means of application controls and/or mobile device camera(s). For example, in an exemplary embodiment, a camera on the mobile device may be used to record the user (who may be a patient) walking so as to record at least one gait cycle of the user. In some embodiments, the user 101 may be a single user or a plurality of users. In some embodiments, mobile device(s) 102 and/or server(s) 103 may be implemented on appropriate computing circuitry platform(s) suitable to perform in accordance with at least some embodiments of the present disclosure. In some embodiments, the exemplary inventive computing system, the exemplary inventive computing device, or the exemplary inventive computing component which may fully or partially reside in mobile device(s) 102 and/or server(s) 103 may generate an output (e.g., gait determination) which may or may not be processed further or/and used in other applications as at least detailed herein and any other similarly suitable applications.

Figure 3:
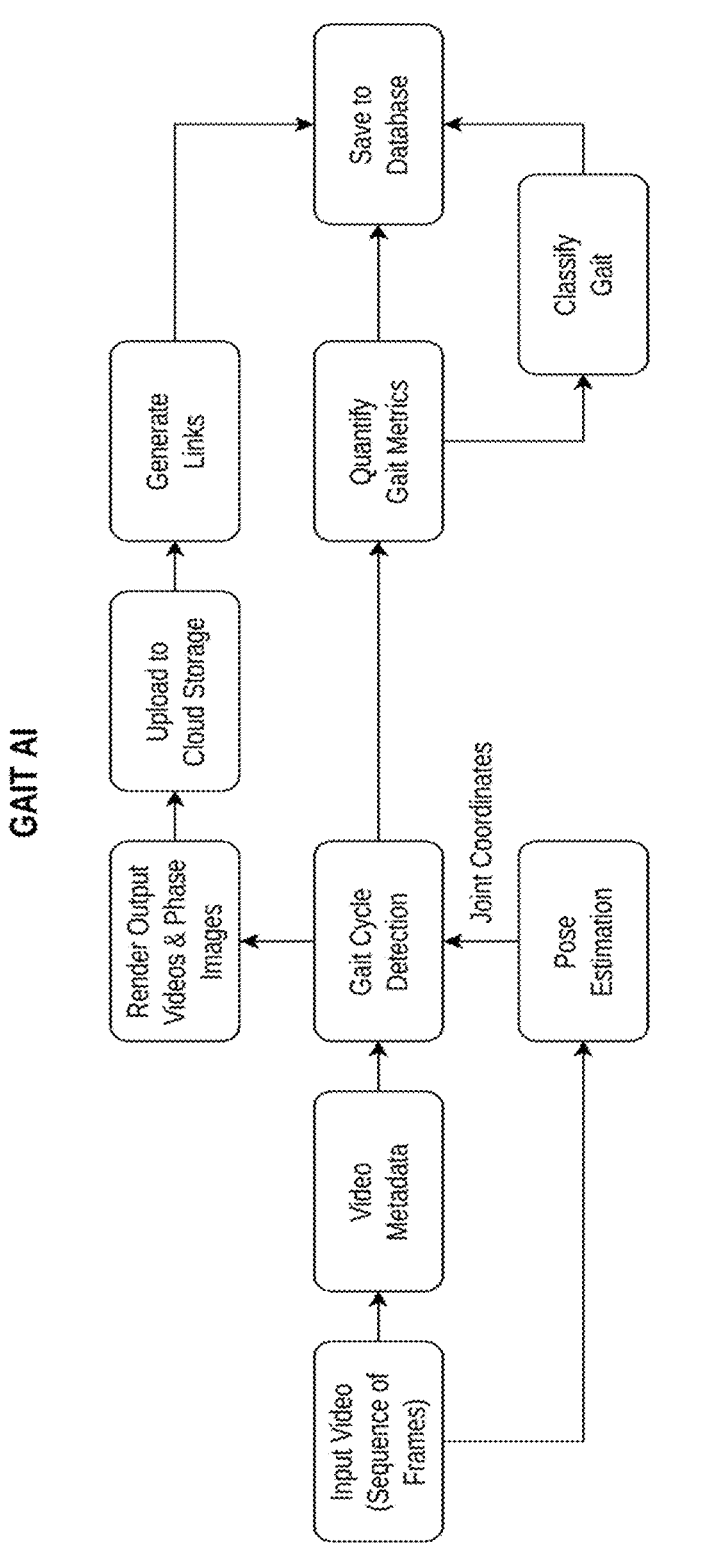
FIG. 3 depicts the architecture of a system for determining whether a patient has normal or abnormal gait according to an exemplary embodiment of the present disclosure.

FIG. 3 depicts the architecture of a system for determining whether a patient has normal or abnormal gait according to an exemplary embodiment of the present disclosure. As shown in FIG. 3, a gait application program interface (API) receives a video from a patient or other user. In the exemplary embodiment of FIG. 3, the video is stored and the process of analyzing the gait sequence is initiated. In the exemplary embodiment of FIG. 3, the video is divided into a sequence of frames, and the video metadata are extracted. In the exemplary embodiment of FIG. 3, next, the Pose estimation is done using our custom-trained models. In the exemplary embodiment of FIG. 3, the output of the Pose Estimation algorithm, namely the coordinates of one or more of the key points described above are fed into the gait cycle detection algorithm along with the video metadata. In the exemplary embodiment of FIG. 3, the images of the important phases are extracted and stored. In the exemplary embodiment of FIG. 3, after the gait cycle detection and the extraction of the gait phase images, a pose skeleton of the patient is drawn on a copy of each frame of the video to create an output video. In the exemplary embodiment of FIG. 3, then, metrics for the gait cycle are calculated as described above, including, for example, the average gait cycle time and the average gait stance time. In the exemplary embodiment of FIG. 3, based on the average gait stance time, the gait sequence is classified as normal or abnormal gait.

Figure 4:
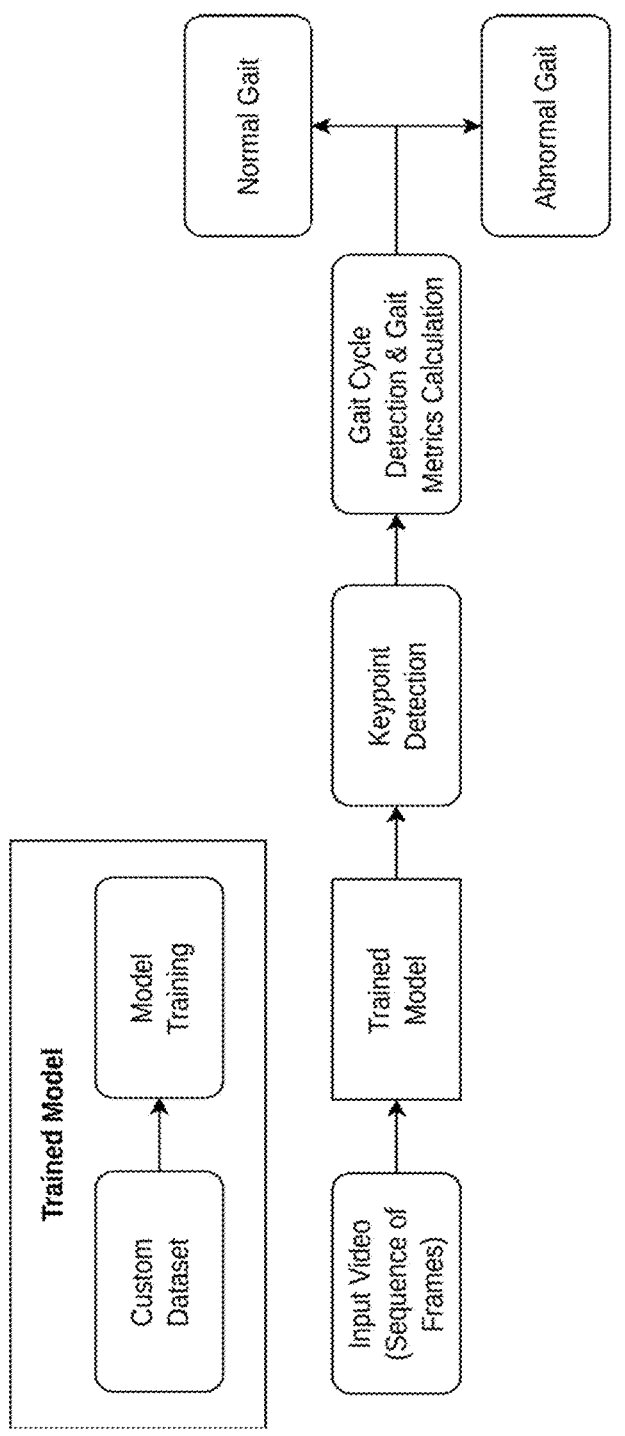
FIG. 4 depicts a flow chart of a method for determining whether a patient has normal or abnormal gait according to an exemplary embodiment of the present disclosure.

FIG. 4 depicts a flow chart of a method for determining whether a patient has normal or abnormal gait according to an exemplary embodiment of the present disclosure. In the exemplary embodiment of FIG. 4, the flow chart depicts details of the gait classification portion of the gait API of FIG. 3. As shown in FIG. 4, in some embodiments, the method includes a plurality of subsystems. In some embodiments, the plurality of subsystems includes a training subsystem (labeled "Train") and an evaluation subsystem, which correspond to the labeled boxes outside of the training subsystem. In some embodiments, the training subsystem may be configured to receive data for training a machine learning model that may be configured to determine whether a patient has normal or abnormal gait. In some embodiments, the evaluation subsystem may be configured to use the trained machine learning model to determine whether a patient has normal or abnormal gait.

Figure 5:
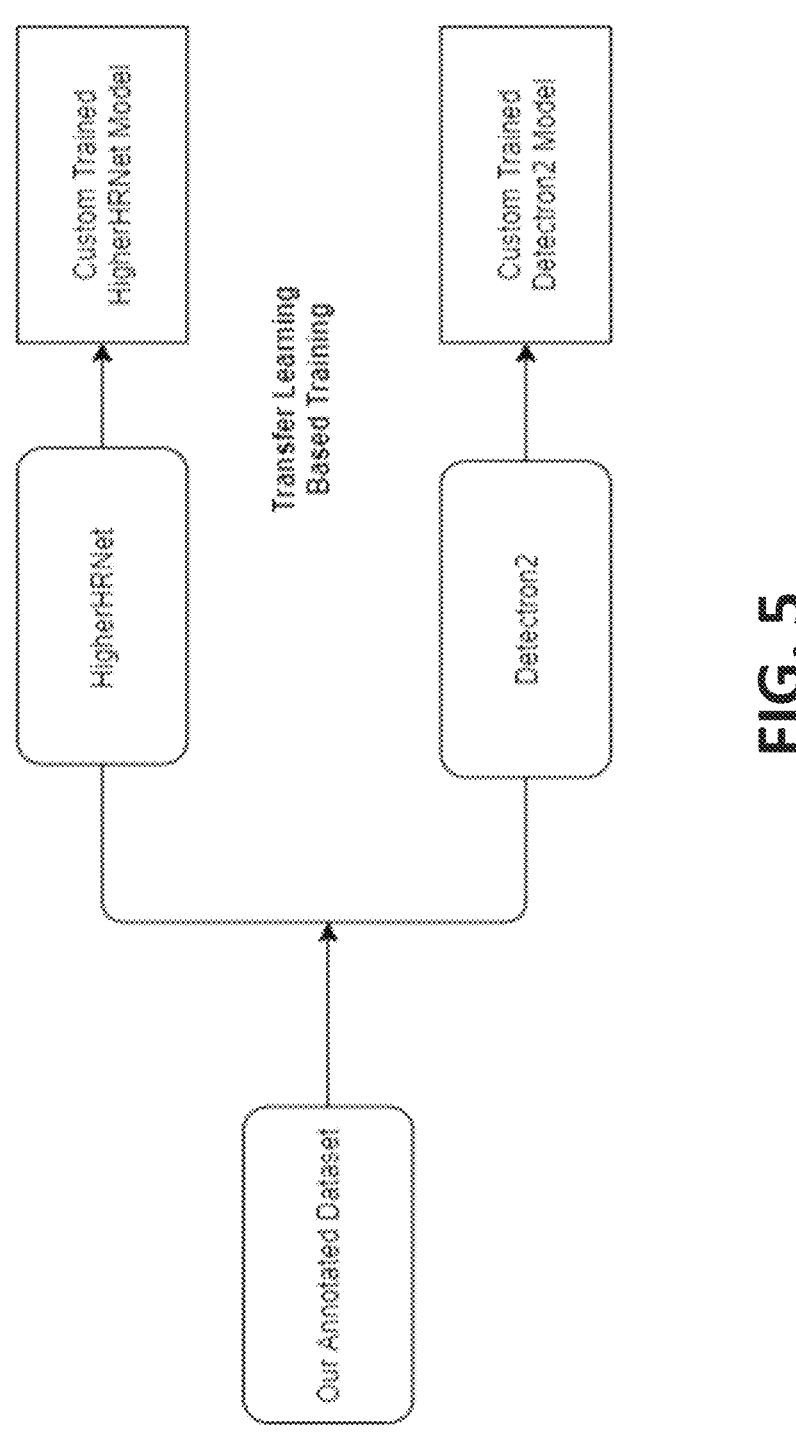
FIG. 5 depicts a flow chart of a training procedure for pose estimation according to an exemplary embodiment of the present disclosure.

FIG. 5 depicts a flow chart of a training procedure for pose estimation according to an exemplary embodiment of the present disclosure. In the exemplary embodiment of FIG. 5, the model may be trained based on the key points described herein. In the exemplary embodiment of FIG. 5, the trained model may be used for pose estimation to extract the coordinates of the key points, along with their confidence scores. In some embodiments, the confidence scores may be related to accuracy of the estimated key points. In the exemplary embodiment of FIG. 5, the training procedure may include custom trained HigherHRNet and Detectron2 models to estimate a first set of key points and a second set of key points.

Figure 6:
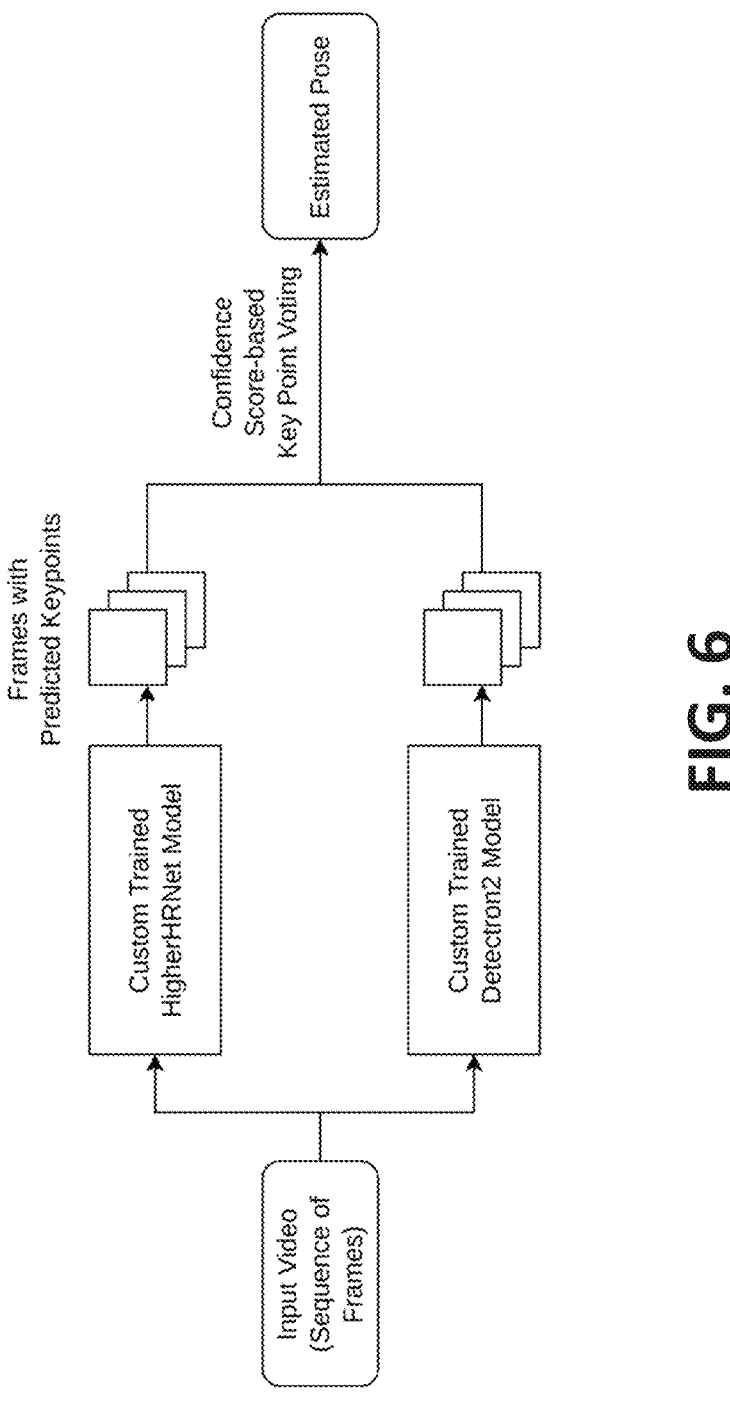
FIG. 6 depicts a flow chart of the pose estimation procedure according to an exemplary embodiment of the present disclosure.

FIG. 6 depicts a flow chart of the pose estimation procedure according to an exemplary embodiment of the present disclosure. In the exemplary embodiment of FIG. 6, each video frame of the input video is copied and fed into our custom-trained models of the exemplary embodiment of FIG. 5. In the exemplary embodiment of FIG. 6, these models return the coordinates of the key points of the body for that frame. In the exemplary embodiment of FIG. 6, the coordinates for the key points may be based on the confidence score for those key points returned by the custom-trained models of the exemplary embodiment of FIG. 6. In the exemplary embodiment of FIG. 6, pose estimation is then accomplished based on key point voting using confidence score.

Figure 7:
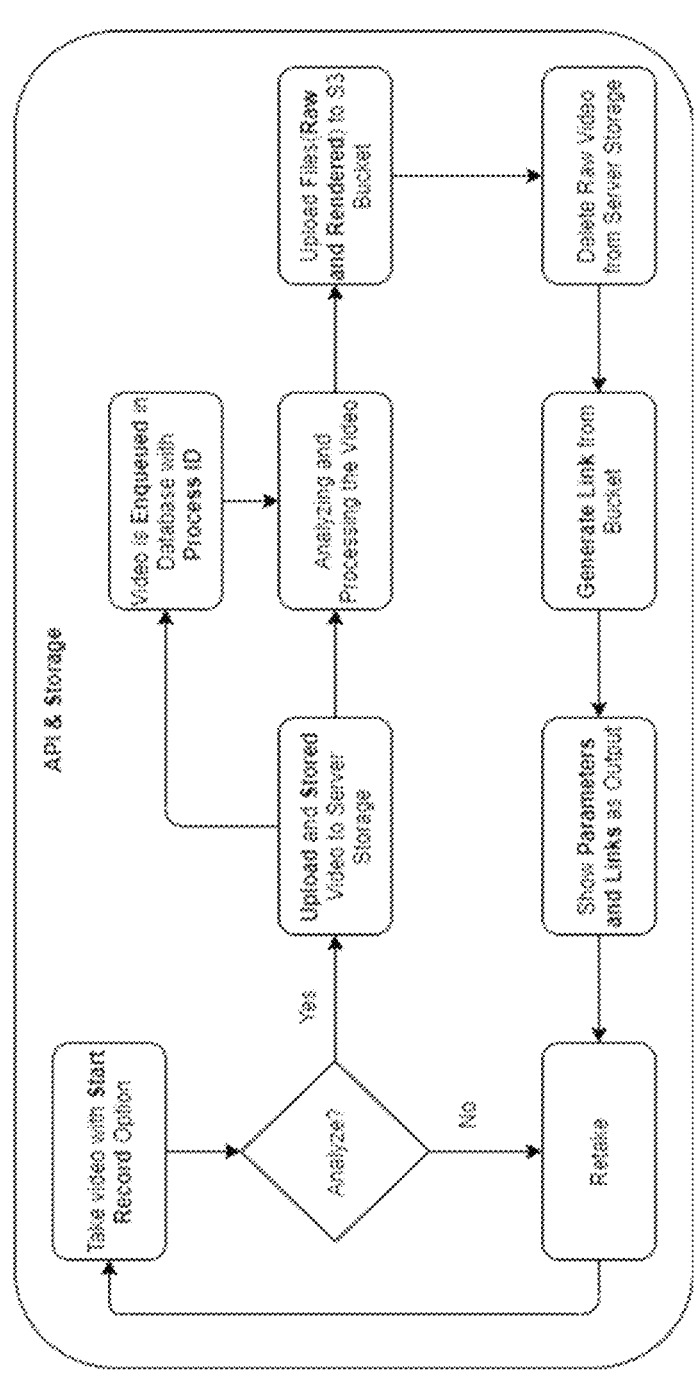
FIG. 7 depicts a flow chart of a gait application programming interface ("API") according to an embodiment of the present disclosure.

FIG. 7 depicts a flow chart of an API for taking and storing videos for gait detection according to an exemplary embodiment of the present disclosure. In the exemplary embodiment of FIG. 7, after the video is recorded, an analysis occurs to determine whether a gait cycle can be detected in the video so that it can be used in a gait detection trained module of the present disclosure. In the exemplary embodiment of FIG. 10, if a gait cycle can be detected in the video, is upload and stored to server storage. In the exemplary embodiment of FIG. 10, the stored video is enqueued in a database with Process ID. In the exemplary embodiment of FIG. 10, if a gait cycle cannot be detected in the video, then the video of the patient may be retaken.

Figure 8:
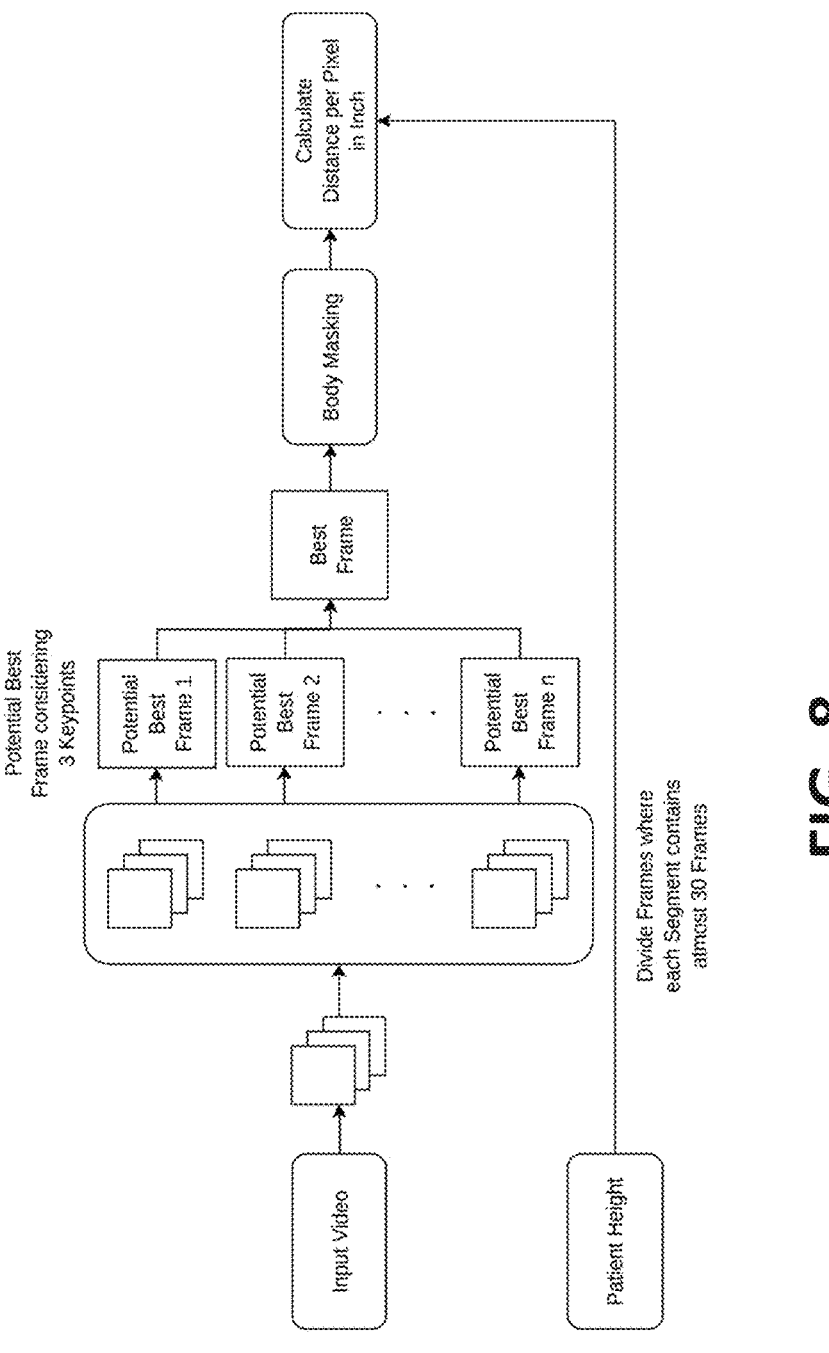
FIG. 8 depicts a flow chart of a calibration procedure according to an exemplary embodiment of the present disclosure.

FIG. 8 depicts a flow chart of an exemplary calibration procedure. In the exemplary calibration procedure, video data is input of the patient's side and of the patient's height. In some embodiments, the video is decomposed into frames. In some embodiments, a voting system based on detection confidence and/or visibility scores is used to determine the best frame. In some embodiments, the best frame is sent to a body masking system to determine the human body segment. In some embodiments, segmented pixels are the human body are used to determine the patient's height. In some embodiments, the calibration procedure includes comparing the segmented pixel height of the patient to the actual height of the patient, and, based on the comparison, calculating lengths of the patient's body parts, e.g., legs, arms, feet, ankles, etc.

Figure 13:
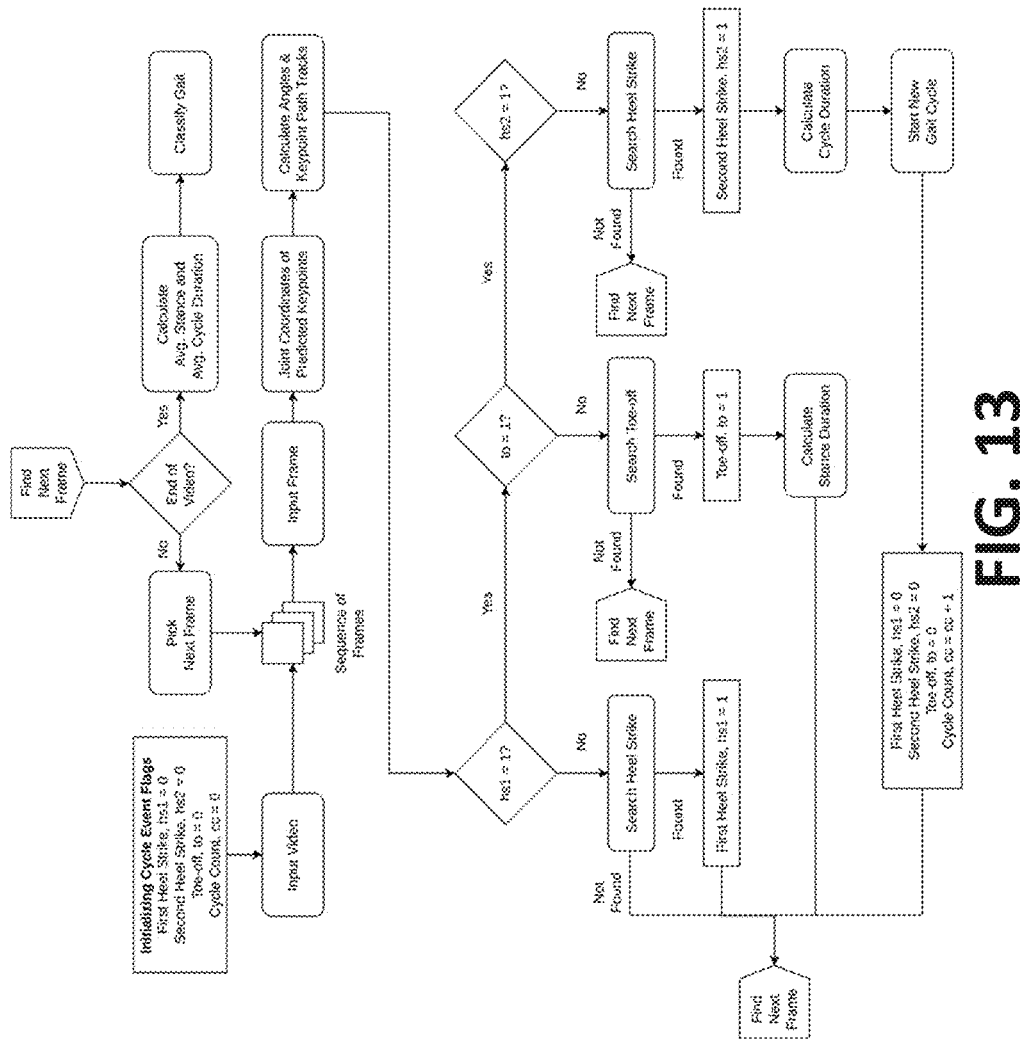
FIG. 13 depicts a flow chart for gait cycle detection and classification according to an exemplary embodiment of the present disclosure.

FIG. 13 depicts a flow chart of an exemplary embodiment for gait cycle detection and classification as described herein. In the exemplary embodiment of FIG. 13, the classification of the gait phases may be done based on the angles at the hip, knee, and the ankle, and the step length specific to the heel strike as described herein. In the exemplary embodiment of FIG. 13, two consecutive heel strikes of the gait of a patient may be considered the beginning and end of that gait cycle. In addition, in the exemplary embodiment of FIG. 13, the interval between the two consecutive heel strikes may be used as a basis of the detection of the gait cycle. In the exemplary embodiment of FIG. 13, the toe-off phase of the gait cycle may be the basis for the detection of the end of the stance phase. In the exemplary embodiment of FIG. 13, after calculating the average duration of the stance and the swing phase, normal or abnormal gait may be classified. For example, in the exemplary embodiment of FIG. 13, if the stance phase of the gait cycle deviated from the standard stance phase duration of approximately 60% of the gait cycle by 10 percent, then the patient may be classified as having abnormal gait.

Variations, modifications and alterations to embodiments of the present disclosure described above will make themselves apparent to those skilled in the art. All such variations, modifications, alterations and the like are intended to fall within the spirit and scope of the present disclosure.

While several embodiments of the present disclosure have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

Any feature or element that is positively identified in this description may also be specifically excluded as a feature or element of an embodiment of the present disclosure.

The disclosure described herein may be practiced in the absence of any element or elements, limitation or limitations, which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure.

What is claimed:

1. A system comprising:
a gait analysis device comprising:
a receiver configured to receive a video of a patient transmitted from a sending device;
a frame extractor configured to extract frames from the video of the patient;
wherein the gait analysis device comprises:
   at least one memory;
   at least one processor configured to use a video of a patient received
   by the receiver and a machine learning model for gait classification,
   wherein the machine learning model is trained by data generated from
      a. a key point trained model configured to generate a set of key points on a patient's body; comprising:
         i. a first key point trained model configured to generate a first set of key points on the patient's body using the extracted frames from the video of the patient;
         ii. a second key point trained model configured to generate a second set of key points on the patient's body using the extracted frames from the video of the patient; and
         iii. a pose estimation model configured to determine a third set of key points, wherein the third set of key points includes key points from the first set of key points and/or key points from the second set of key points;
      b. an Angle-Based Approach configured to use at least one of the first set of key points and the second set of key points to classify the patient's gait based on angle calculations between at least two key points; and
      c. a Key Point Path Track-Based Approach configured to use at least one of the first set of key points and the second set of key points to classify the patient's gait based on a patient's stance phase and swing phase; and a display to output the gait classification.

2. The system of claim 1, wherein the first key point trained model is different from the second key point trained model.

3. The system of claim 1, wherein the first set of key points and the second set of key points each comprise at least two of the following key points: a key point for the nose, the left eye, the right eye, the left ear, the right ear, the left shoulder, the right shoulder, the left elbow, the right elbow, the left wrist, the right wrist, the left hip, the right hip, the left knee, the right knee, the left ankle, the right ankle, the left big toe, the right big toe, the left little toe, the right little toe, the left heel, or the right heel, or any combination thereof.

4. The system of claim 3, wherein the angle calculations between the at least two key points include at least one of hip flexion, knee flexion, hip extension, knee extension, plantarflexion, dorsiflexion, or any combination thereof.

5. The system of claim 3, wherein the at least two key points include the right ankle key point and the left ankle key point, and wherein the Key Point Path Track-Based Approach is configured to use signals detected for speed of the right ankle key point and the left ankle key point to classify the patient's gait based on a patient's stance phase and swing phase.

6. The system of claim 3, wherein the at least two key points include the right ankle key point and the left ankle key point, and wherein the Key Point Path Track-Based Approach is configured to use signals detected of the distance between x-coordinates of ankle key points to classify the patient's gait based on a patient's stance phase and swing phase.

7. A method comprising:
obtaining a gait analysis device;
receiving a video of a patient on the gait analysis device;
extracting frames from the video of the patient using a frame extractor on the gait analysis device;
classifying the patient's gait using a video of a patient received by the receiver and a machine learning model on the gait analysis device;
wherein the machine learning model is trained by data generated from:
   a. a key point trained model configured to generate a set of key points on a patient's body; comprising:
      i. a first key point trained model configured to generate a first set of key points on the patient's body using the extracted frames from the video of the patient;
      ii. a second key point trained model configured to generate a second set of key points on the patient's body using the extracted frames from the video of the patient; and
      iii. a pose estimation model configured to determine a third set of key points, wherein the third set of key points includes key points from the first set of key points and/or key points from the second set of key points;

b. an Angle-Based Approach configured to use at least one of the first set of key points and the second set of key points to classify the patient's gait based on angle calculations between at least two key points; and c. a Key Point Path Track-Based Approach configured to use at least one of the first set of key points and the second set of key point to classify the patient's gait based on a patient's stance phase and swing phase; and displaying the gait classification.

8. The method of claim 7, wherein the first key point trained model is different from the second key point trained model.

9. The method of claim 7, wherein the first set of key points and the second set of key points each comprise at least two of the following key points: a key point for the nose, the left eye, the right eye, the left ear, the right ear, the left shoulder, the right shoulder, the left elbow, the right elbow, the left wrist, the right wrist, the left hip, the right hip, the left knee, the right knee, the left ankle, the right ankle, the left big toe, the right big toe, the left little toe, the right little toe, the left heel, the right heel, or any combination thereof.

10. The method of claim 9, wherein the angle calculations between the at least two key points include at least one of hip flexion, knee flexion, hip extension, knee extension, plantar-flexion, dorsiflexion, or any combination thereof.

11. The method of claim 9, wherein the at least two key points include the right ankle key point and the left ankle key point, and wherein the Key Point Path Track-Based Approach is configured to use signals detected for speed of the right ankle key point and the left ankle key point to classify the patient's gait based on a patient's stance phase and swing phase.

12. The method of claim 9, wherein the at least two key points include the right ankle key point and the left ankle key point, and wherein the Key Point Path Track-Based Approach is configured to use signals detected of the distance between x-coordinates of ankle key points to classify the patient's gait based on a patient's stance phase and swing phase.

\* \* \* \* \*